United States Patent
Kim et al.

(10) Patent No.: US 9,850,509 B2
(45) Date of Patent: Dec. 26, 2017

(54) OLEAGINOUS MICROORGANISM DISRUPTION PROCESS USING SUPERSONIC DISPERSER AND METHOD FOR PRODUCING BIO-OIL USING SAME

(71) Applicants: SK Innovation Co., Ltd., Seoul (KR); SK Global Chemical Co., Ltd., Seoul (KR)

(72) Inventors: Chang Kuk Kim, Daejeon (KR); Yeon Hwa La, Daejeon (KR); Joong Min Park, Daejeon (KR); Hong Seung Yeon, Cheongju-si (KR); Cher Hee Park, Seoul (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 14/905,326

(22) PCT Filed: Dec. 20, 2013

(86) PCT No.: PCT/KR2013/011927
§ 371 (c)(1),
(2) Date: Jan. 15, 2016

(87) PCT Pub. No.: WO2015/064835
PCT Pub. Date: May 7, 2015

(65) Prior Publication Data
US 2016/0160246 A1 Jun. 9, 2016

(30) Foreign Application Priority Data
Nov. 1, 2013 (KR) .......................... 10-2013-0131925

(51) Int. Cl.
*C12P 7/64* (2006.01)
*C11B 1/02* (2006.01)
*C12N 13/00* (2006.01)
*C11B 3/00* (2006.01)
*C12M 1/00* (2006.01)

(52) U.S. Cl.
CPC .............. *C12P 7/6427* (2013.01); *C11B 1/02* (2013.01); *C11B 3/005* (2013.01); *C12M 21/02* (2013.01); *C12M 47/06* (2013.01); *C12P 7/6472* (2013.01)

(58) Field of Classification Search
None
See application file for complete search history.

(56) References Cited

U.S. PATENT DOCUMENTS

| | | | |
|---|---|---|---|
| 2002/0001833 A1 | 1/2002 | Ruecker et al. | |
| 2009/0137015 A1 | 5/2009 | Skudder | |

FOREIGN PATENT DOCUMENTS

| | | | | |
|---|---|---|---|---|
| JP | 2010-082574 A | | 4/2010 | |
| JP | 2010082574 A | * | 4/2010 | |
| JP | 2010-187645 A | | 9/2010 | |
| KR | 10-2003-0013367 A | | 2/2003 | |
| KR | 10-1303617 B1 | | 4/2012 | |
| KR | 10-2013-0014091 A | | 2/2013 | |
| KR | 10-1251191 B1 | | 4/2013 | |
| KR | 10-1317242 B1 | | 10/2013 | |
| KR | 101317242 B1 | * | 10/2013 | |

OTHER PUBLICATIONS

Thevenieau et al., "Microorganisms as sources of oils", Oilseeds & fats, Crops and Lipids 2013, vol. 20, D603, pp. 1-8.*
Adam et al.""Solvent-free" ultrasound-assisted extraction of lipids from fresh microalgae cells: A green, clean and scalable process", Bioresource Technology 2012, vol. 114, pp. 457-465.*

* cited by examiner

*Primary Examiner* — Michelle F Paguio Frising
(74) *Attorney, Agent, or Firm* — The Webb Law Firm

(57) ABSTRACT

Provided are an oleaginous microorganism disruption process using a supersonic disperser and a method for producing bio-oil using the same. The method for producing bio-oil according to the present invention induces a cell disruption of oleaginous microorganisms without a separate drying process, thereby providing a method for continuously producing bio-oil in an economical and simple manner. In addition, the method of the present invention induces a cell disruption of oleaginous microorganisms without a heating process, thereby producing bio-oil without a change in physical properties due to the heat.

13 Claims, 6 Drawing Sheets

[FIG. 1]
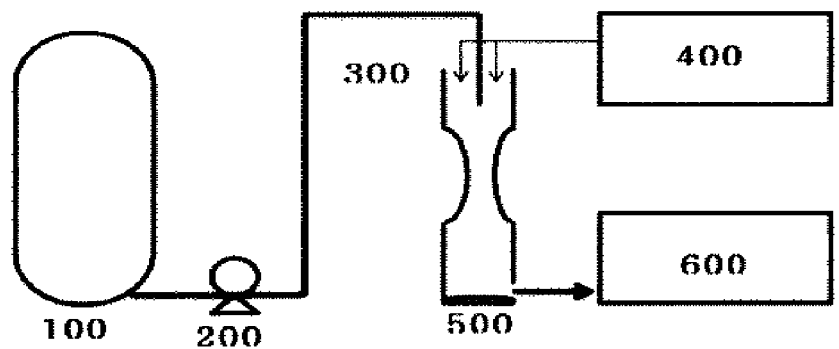

[FIG. 2]
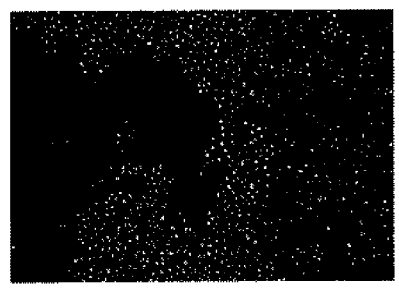

[FIG. 3]

[FIG. 4]

[FIG. 5]
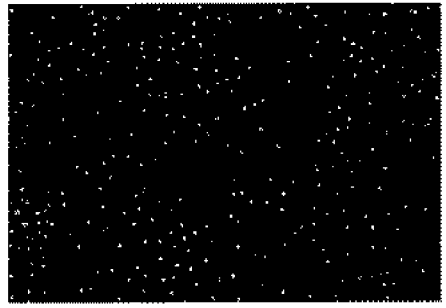

[FIG. 6]

OLEAGINOUS MICROORGANISM DISRUPTION PROCESS USING SUPERSONIC DISPERSER AND METHOD FOR PRODUCING BIO-OIL USING SAME

CROSS-REFERENCE TO RELATED APPLICATIONS

This application is the United States national phase of International Application No. PCT/KR2013/011927 filed Dec. 20, 2013, and claims priority to Korean Patent Application No. 10-2013-0131925 filed Nov. 1, 2013, the disclosures of which are hereby incorporated in their entirety by reference.

TECHNICAL FIELD

The present invention relates to an oleaginous microorganism disruption process using a supersonic disperser and a method for producing bio-oil using the same.

More particularly, the present invention relates to an oleaginous microorganism disruption process using a supersonic disperser and a method for producing bio-oil using the same capable of saving energy costs involved by a water removal process and achieving a high disruption rate, by impinging the oleaginous microorganism on a disruption plate of the supersonic disperser to induce a cell disruption.

BACKGROUND ART

Oleaginous microorganism is microorganism producing bio-oil using unicellular photosynthetic organisms which may be photo-synthetically grown using water, carbon dioxide, and sunlight or chemicals such as sugar, organic acid, and low molecular alcohol.

The oleaginous microorganism may be cultivated anywhere like a waste land, a coast, and an ocean if there are organic materials which may be photosynthetically grown or may be used as feed and live in freshwater, brackis water, or sea water at a size of 0.5 to 30 µm and contain useful materials such as oil and antioxidant. In particular, the oleaginous microorganism has a good quality of bio-oil accumulated therein and has oil production per unit area at least 10 times higher, at most 100 times higher, and about 50 to 100 times higher than edible plants such as bean and rape plant for obtaining the existing raw oil for bio diesel.

Further, the oleaginous microorganism has a growth rate faster than land plants and may be cultivated in mass production at a high concentration and may be grown even under the extreme environment.

In addition, the oleaginous microorganism demonstrates fuel productivity higher than the existing corps since a usable oil component reaches 30 to 70% of bio mass. Further, the oleaginous microorganism does not compete with other plants in terms of a ground or a space, and therefore does not cause secondary environmental problems such as price increase of food resource and deforestation.

Accordingly, a technology of producing bio-diesel using the oleaginous microorganism has high productivity per unit area to easily secure resources and does not compete with a food resource and thus may be considered to be adequate for domestic circumference in Korea.

Meanwhile, as a method for extracting raw oil for bio-diesel from the oleaginous microorganism, a one-step solvent extraction method has been mostly used. The solvent extraction method separates oil into a solvent phase from the oleaginous microorganism by using an extracted solvent which may dissolve oil from components of the oleaginous microorganism well and has a slight difference in an extraction yield depending on a kind of used solvent but has limited extraction efficiency and extracts a large amount of microorganism bio-element impurities together at the time of extraction of oil to remarkably reduce conversion efficiency into a bio-diesel.

Therefore, technologies of disrupting a cell of oleaginous microorganism using methods such as microwave pre-treatment (Korean Patent Laid-Open Publication No. 2013-0014091), ultrasonic treatment using sonication (Japanese Patent Laid-Open Publication No. 2010-187645), electro beam treatment, plasma treatment, etc., prior to extracting raw oil for bio-diesel from oleaginous microorganism have been well known.

However, in extracting the bio-oil from the oleaginous microorganism by an oleaginous microorganism disruption process based on the technologies, complex processes such as a separate process of removing moisture and a process of giving cooling conditions to cope with occurrence of flames need to be additionally performed and the oleaginous microorganism is denaturalized by heat to cause the degradation in quality of product oil, etc.

DISCLOSURE

Technical Problem

An object of the present invention is to provide an oleaginous microorganism disruption process and a method for producing bio-oil using the same capable of inducing a cell disruption of the cultivated oleaginous microorganism using a supersonic disperser without a drying process, saving energy costs involved by a water removal process, and having a high disruption ratio.

Another object of the present invention is to provide an oleaginous microorganism disruption process which does not cause a change in physical properties due to heat and is suitable for a continuous flow system, by inducing a cell disruption without a separate heating process to induce a cell disruption of the oleaginous microorganism.

Technical Solution

In one general aspect, a method for producing bio-oil includes: cultivating oleaginous microorganism; ultrasonically accelerating the cultivated oleaginous microorganism using gas to disrupt the oleaginous microorganism; and extracting the bio-oil from the disrupted oleaginous microorganism.

Advantageous Effects

According to the exemplary embodiments of the present invention, it is possible to provide the method for producing bio-oil which is economical and little denaturalizes the oleaginous microorganism by inducing the cell disruption without performing the drying or heating treatment process on the oleaginous microorganism.

Further, it is possible to provide the oleaginous microorganism disruption process and the method for producing bio-oil capable of improving the extraction efficiency of the bio-oil by increasing the cell disruption efficiency of the oleaginous microorganism by the heat insulation expansion involved by the ultrasonic acceleration of the culture medium including the oleaginous microorganism.

DESCRIPTION OF DRAWINGS

FIG. 1 is a diagram schematically illustrating an oleaginous microorganism disruption process and a method for producing bio-oil using the same according to an exemplary embodiment of the present invention.

FIG. 2 is a photomicrograph of the oleaginous microorganism prior to being disrupted.

FIG. 3 is a photomicrograph of a disruption solution according to a disruption process using the supersonic disperser.

FIG. 4 is a photomicrograph of a disruption solution according to a disruption process using an ultrahomogenizer.

FIG. 5 is a photomicrograph of a disruption solution according to a disruption process using a microwave.

FIG. 6 is a photomicrograph of a solution disrupted by a disruption process using ultrasonication.

DETAILED DESCRIPTION OF MAIN ELEMENTS

100: Oleaginous microorganism fermentor
200: Culture medium transfer pump
300: Acceleration nozzle part of supersonic disperser
400: Gas compression and high-pressure supply part
500: Oleaginous microorganism impinging plate
600: Bio-oil extracting and separating part

BEST MODE

The present invention relates to a method for producing bio-oil from oleaginous microorganism and may provide a method for producing bio-oil in an economical and simple manner without separate dewatering/heating processes by ultrasonically accelerating the oleaginous microorganism using gas supplied from a high-pressure supply part to disrupt the oleaginous microorganism.

Hereinafter, an oleaginous microorganism disruption process using a supersonic disperser and a method for producing bio-oil using the same according to the present invention will be described in detail with reference to the accompanying drawings and embodiments, but the following drawings and embodiments are only embodiments which are limited to the gist of the present invention.

Meanwhile, it is apparent to those skilled in the art that the present invention is not limited to process conditions proposed by the following embodiments but may be arbitrarily selected within a range required to achieve the objects of the present invention.

The present invention relates to a method for producing bio-oil using oleaginous microorganism. The method for producing bio-oil includes: cultivating oleaginous microorganism; ultrasonically accelerating the cultivated oleaginous microorganism using gas to disrupt the oleaginous microorganism; and extracting the bio-oil from the disrupted oleaginous microorganism.

The cultivating of the oleaginous microorganism according to the exemplary embodiment of the present invention includes all the cultivation methods suitable for the method for producing bio-oil according to the exemplary embodiment of the present invention.

For example, in the cultivating, the oleaginous microorganism may be cultivated in an oleaginous microorganism fermentor based on batch, fed-batch, and continuous cultivation manners. In terms of a mass production of the oleaginous microorganism using the continuous cultivation manner, the fed-batch or continuous fermentor is preferable.

To cultivate the oleaginous microorganism using the fed-batch or continuous fermentor, it is preferable to supply a carbon source.

In this case, any carbon source may be used without limitation as long as it may be grown using the oleaginous microorganism. An example of the carbon source may preferably include glucose, fructose, sucrose, galactose, glycerol, crude glycerol which is a bio diesel wastes, etc., but the carbon source is not limited thereto. Herein, the glucose is most preferable.

The carbon source is preferably supplied in the continuous or fed-batch manner to be maintained at an appropriate concentration. If necessary, a method such as pH-stat and DO-stat may be used and a method for measuring concentrations of each carbon source in real time and supplying the carbon sources if necessary, and the like may also be used.

Further, nutritive components required to grow the oleaginous microorganism may be included in a medium. Here, it is apparent to those skilled in the art that various kinds of nitrogen sources, phosphate sources, other components, and the like may be included in the medium and a complex medium, a defined medium, or the like may be used.

As the nitrogen source, organic nitrogen sources such as yeast extract, corn steep liquor, beef extract, malt extract, peptone, and tryptone or inorganic nitrogen sources such as ammonium acetate, ammonium nitrate, ammonium sulfate, sodium nitrate, and urea may also be used. In particular, an operation is preferably performed within a range of an appropriately set salt concentration.

Further, it is preferable to maintain pH and/or temperature in a preset range while the oleaginous microorganism is cultivated by the fed-batch or continuous manner.

As a method for constantly maintaining pH and/or temperature during the cultivation, the method well known in the art may be used. For example, a method for using a cooling jacket using cooling water, a method for automatically supplying acid and base using a pH controller, etc., may be used but the present invention is not limited thereto.

The cultivation of the oleaginous microorganism by the fed-batch or continuous cultivation manner is preferably made under appropriate aeration and agitation of air.

In more detail, the oleaginous microorganism is aerobic and is weak against a shearing stress generated by the agitation. Therefore, an agitation speed may be 50 to 300 rpm, preferably 100 to 300 rpm and a supply speed of air may be 0.5 to 5 vvm, preferably 1 to 3 vvm.

The method for producing bio-oil according to the exemplary embodiment of the present invention ultrasonically accelerates the cultivated oleaginous microorganism using gas to disrupt a cell wall of the oleaginous microorganism.

As the existing method for disrupting a cell wall to produce the bio-oil using the oleaginous microorganism, heat treatment, simple compression, cell disruption by ferment, microwave pre-treatment, electro-beam irradiation, sonication, plasma treatment, etc., are used. However, the methods include a dewatering and/or drying process of removing moistures, which leads to a problem of economic views, a change in physical properties of bio-oil due to a heating process, etc.

However, the disruption process according to the exemplary embodiment of the present invention ultrasonically accelerates the cultivated oleaginous microorganism using gas to disrupt the cultivated oleaginous microorganism, thereby producing the bio-oil from the oleaginous microorganism without the separate drying process, achieving a high disruption rate, and requiring less time.

In more detail, all devices which may ultrasonically accelerate the oleaginous microorganism to disrupt the oleaginous microorganism may be used for the disruption process according to the exemplary embodiment of the present invention. For example, the supersonic disperser may be used.

FIG. 1 is a diagram schematically illustrating an oleaginous microorganism disruption process and a method for producing bio-oil according to the exemplary embodiment of the present invention. The oleaginous microorganism which is cultivated by an oleaginous microorganism fermentor 100 may be injected into an acceleration nozzle part 300 of a supersonic disperser using a culture medium transfer pump 200 and the cultivated oleaginous microorganism injected into the acceleration nozzle part 300 may be ultrasonically accelerated by high-pressure gas supplied from a high-pressure supply part 400 in which compressed gas is present, impinge on an impinging plate 500 within the supersonic disperser, and then be disrupted.

The disrupted oleaginous microorganism disruption solution passes through an extraction and separation process part 600 and then may be used in the production of the bio-oil.

Therefore, the supersonic disperser which may be used to disrupt the oleaginous microorganism according to the exemplary embodiment of the present invention may include the oleaginous microorganism impinging plate 500 and the high-pressure supply part 400 which may inject gas into the acceleration nozzle part 300 at a high pressure.

That is, the exemplary embodiment of the present invention may be a method for producing bio-oil by allowing the cultivated oleaginous microorganism to impinge on the impinging plate 500 using the supersonic disperser under the presence of gas to disrupt the cultivated oleaginous microorganism.

Further, the supersonic disperser used in the disruption process according to the exemplary embodiment of the present invention includes the high-pressure supply part 400 which may inject gas into the acceleration nozzle at a high pressure.

The pressure of the high-pressure supply part 400 according to the exemplary embodiment of the present invention may be maintained so that the gas injected into the acceleration nozzle part 300 of the supersonic disperser is maintained at a high pressure enough to ultrasonically accelerate the oleaginous microorganism.

In more detail, the pressure in the high-pressure supply part 400 may be 1 to 2 MPa.

The oleaginous microorganism disruption process according to the exemplary embodiment of the present invention directly injects the oleaginous microorganism cultivated by the fermentor 100 into the acceleration nozzle part 300 by the culture medium transfer pump 200 without the separate drying process, thereby continuously producing the bio-oil from the oleaginous microorganism in an economical and simple process condition.

The gas used in the disruption process according to the exemplary embodiment of the present invention may be inert gas or active gas, and therefore any gas may be used as long as gas may achieve the object of the present invention. Preferably, air, nitrogen, carbon dioxide, helium, etc., may be used.

In the disruption process according to the exemplary embodiment of the present invention, the supply speed of gas injected into the acceleration nozzle part 300 of the supersonic disperser is enough to ultrasonically accelerate the oleaginous microorganism under the high pressure condition.

In more detail, the supply speed of gas injected into the acceleration nozzle part 300 of the supersonic disperser in the high-pressure supply part 400 according to the exemplary embodiment of the present invention may be 0.5 to 3 MPa, more preferably 1 to 2 MPa.

As the impinging plate 500 according to the exemplary embodiment of the present invention, a metal plate which has a large disruption effect of the oleaginous microorganism, no disruptions deposited thereon, and a smooth surface. Preferably, a surface of the metal plate is coated with diamond, thereby increasing strength against impingement and abrasion.

As described above, the disruption process according to the exemplary embodiment of the present invention ultrasonically accelerates the oleaginous microorganism using gas to induce the reduction in temperature due to the heat insulation expansion and allows the oleaginous microorganism to impinge on the impinging plate in the state in which a cell surface of the oleaginous microorganism is hard to generate an impulsive force and/or a shearing force, etc., thereby achieving a disruption rate higher than that of other disruption processes.

The oleaginous microorganism which goes through the disruption process according to the exemplary embodiment of the present invention may go through the extracting of the bio-oil. All the methods for extracting bio-oil which may achieve the object of the present invention may be used. Among those, a solvent extraction method using a solvent is preferable.

In the oleaginous microorganism disruption solution which goes through the disruption process according to the exemplary embodiment of the present invention, the disruption rate of the cell wall is very high and therefore an amount of bio-oil which may be extracted by the solvent extraction method may be more increased than the other existing disruption and extraction processes.

As the extraction solvent used in the extraction process according to the exemplary embodiment of the present invention, an organic solvent is preferable. Herein, a polar organic solvent and a non-polar organic solvent may be used without any limitation as long as the extraction solvent is a kind of organic solvent.

For example, the extraction solvent may be any one selected from a group consisting of hexane, methanol, ethanol, butanol, isopropanol, chloroform, acetone, and acetonitrile, and a mixture thereof.

In addition, the solvent extraction method may be performed by a soxhlet extraction device, an agitation extraction device, etc., but is not limited thereto. Therefore, any device which may achieve the object of the present invention may be used without limitation.

An extraction solution including the oleaginous microorganism which goes through the disruption process and the extraction process according to the exemplary embodiment of the present invention may be separated into an oil phase including the bio-oil and an aqueous phase including the cell disruptions and the bio-oil may be produced by recovering and purifying only the oil phase after the extraction process is completed.

The method for producing bio-oil according to the exemplary embodiment of the present invention may be the method for producing bio-oil which further includes separating the oil phase from the aqueous phase in the oleaginous microorganism extraction solution which goes through the disrupting and the extracting.

The extracted and separated material is the bio-oil prior to being purified and the final bio-oil product may be acquired by a series of bio-oil purifying processes.

That is, the present invention may be the method for producing bio-oil which further includes purifying the extracted and separated bio-oil.

The bio-oil produced from the oleaginous microorganism according to the exemplary embodiment of the present invention preferably includes a large amount of omega-3 unsaturated fatty acid, more preferably contains omega-6 unsaturated fatty acid in addition to the large content of omega-3 unsaturated fatty acid.

Therefore, the purifying of the bio-oil which goes through the extracting and the separating according to the exemplary embodiment of the present invention may include all the processes of producing the final bio-oil products containing a large amount of omega-3 unsaturated fatty acid and omega-6 unsaturated fatty acid.

As a non-restrictive example, the purifying of the bio-oil according to the exemplary embodiment of the present invention includes at least one selected from removing coagulated oil, bleaching using at least one of bleaching clay and active carbon, filtering, and deodorizing.

In more detail, in the purifying of the bio-oil according to the exemplary embodiment of the present invention, the removing of the coagulated oil removes the coagulated oil using silica gel, etc. For example, the coagulated oil may be removed by being left at a temperature condition of −5 to 0° C. for 5 to 20 hours.

Further, in the bleaching, the bio-oil which goes through the extracting and the separating may be purified using at least any one selected from bleaching clay, active carbon, kaolinite, zeolite, and bentonite.

In the bleaching, the used materials may serve as an adsorbent and may also serve to remove humidity, smell, and pollutants such as heavy metal.

The filtering may be performed using a filter having a pore size of 0.5 to 1 μm and the deodorizing may be performed by a pressure-reducing vapor deodorizing process but is not limited thereto.

The final bio-oil product produced by the purifying of the bio-oil according to the exemplary embodiment of the present invention may contain a large amount of omega-3 unsaturated fatty acid and omega-6 unsaturated fatty acid. Preferably, the omega-3 unsaturated fatty acid and the omega-6 unsaturated fatty acid may be equal to or more than 30 wt % in of a total content of bio-oil, more preferably, equal to or more than 40 wt %, and most preferably, equal to or more than 50 wt %.

The oleaginous microorganism cultivating process and the oleaginous microorganism disrupting process using a supersonic disperser according to the example of the present invention and the method for bio-oil using the same will be described below, but the following examples embodiment is only example of the technical spirit of the present invention and therefore it is apparent to those skilled in the art that the scope of the present invention is not limited to the following exemplary embodiments.

The present invention relates to a method for producing bio-oil using oleaginous microorganism. The method for producing bio-oil includes: cultivating oleaginous microorganism; ultrasonically accelerating the cultivated oleaginous microorganism using gas to disrupt the oleaginous microorganism; and extracting the bio-oil from the disrupted oleaginous microorganism.

The cultivating of the oleaginous microorganism according to the exemplary embodiment of the present invention includes disrupting the oleaginous microorganism and extracting bio-oil, thereby including all cultivation methods for purifying bio-oil.

For example, in the cultivating, the oleaginous microorganism may be cultivated in an oleaginous microorganism fermentor based on batch, fed-batch, and continuous cultivation manners. In terms of a mass production of the oleaginous microorganism using the continuous cultivation manner, the fed-batch or continuous fermentor is preferable.

To cultivate the oleaginous microorganism using the fed-batch or continuous fermentor, it is preferable to supply a carbon source.

In this case, any carbon source may be used without limitation as long as it may be grown using the oleaginous microorganism. An example of the carbon source may preferably include glucose, fructose, sucrose, galactose, glycerol, crude glycerol which is a bio diesel wastes, etc., but the carbon source is not limited thereto. Herein, the glucose is most preferable.

The carbon source is preferably supplied in the continuous or fed-batch manner to be maintained at an appropriate concentration. If necessary, a method such as pH-stat and DO-stat may be used and a method for measuring concentrations of each carbon source in real time and supplying the carbon sources if necessary, and the like may also be used.

Further, nutritive components required to grow the oleaginous microorganism may be included in a medium. Here, it is apparent to those skilled in the art that various kinds of nitrogen sources, phosphate sources, other components, and the like may be included in the medium and a complex medium, a defined medium, or the like may be used.

As the nitrogen source, organic nitrogen sources such as yeast extract, corn steep liquor, beef extract, malt extract, peptone, and tryptone or inorganic nitrogen sources such as ammonium acetate, ammonium nitrate, ammonium sulfate, sodium nitrate, and urea may also be used. In particular, an operation is preferably performed within a range of an appropriately set salt concentration.

Further, it is preferable to maintain pH and/or temperature in a preset range while the oleaginous microorganism is cultivated by the fed-batch or continuous manner.

As a method for constantly maintaining pH and/or temperature during the cultivation, the method well known in the art may be used. For example, a method for using a cooling jacket using cooling water, a method for automatically supplying acid and base using a pH controller, etc., may be used but the present invention is not limited thereto.

The cultivation of the oleaginous microorganism by the fed-batch or continuous cultivation manner is preferably made under appropriate aeration and agitation of air.

In more detail, the oleaginous microorganism is aerobic and is weak against a shearing stress generated by the agitation. Therefore, an agitation speed may be 50 to 300 rpm, preferably 100 to 300 rpm and a supply speed of air may be 0.5 to 5 vvm, preferably 1 to 3 vvm.

The method for producing bio-oil according to the exemplary embodiment of the present invention ultrasonically accelerates the cultivated oleaginous microorganism using gas to disrupt a cell wall of the oleaginous microorganism.

As the existing method for disrupting a cell wall to produce the bio-oil using the oleaginous microorganism, heat treatment, simple compression, cell disruption by ferment, microwave pre-treatment, electro-beam irradiation, sonication, plasma treatment, etc., are used. However, the methods include a dewatering and/or drying process of removing moistures, which leads to a problem of economic views, a change in physical properties of bio-oil due to a heating process, etc.

However, the disruption process according to the exemplary embodiment of the present invention ultrasonically accelerates the cultivated oleaginous microorganism using gas to disrupt the cultivated oleaginous microorganism, thereby producing the bio-oil from the oleaginous microorganism without the separate drying process, achieving a high disruption rate, and requiring less time.

In more detail, all devices which may ultrasonically accelerate the oleaginous microorganism to disrupt the oleaginous microorganism may be used for the disruption process according to the exemplary embodiment of the present invention. For example, the supersonic disperser may be used.

FIG. 1 is a diagram schematically illustrating an oleaginous microorganism disruption process and a method for producing bio-oil according to the exemplary embodiment of the present invention. The oleaginous microorganism which is cultivated by an oleaginous microorganism fermentor 100 may be injected into an acceleration nozzle part 300 of a supersonic disperser using a culture medium transfer pump 200 and the cultivated oleaginous microorganism injected into the acceleration nozzle part 300 may be ultrasonically accelerated by high-pressure gas supplied from a high-pressure supply part 400 in which compressed gas is present, impinge on an impinging plate 500 within the supersonic disperser, and then be disrupted.

The disrupted oleaginous microorganism disruption solution passes through an extraction and separation process part 600 and then may be used in the production of the bio-oil.

Therefore, the supersonic disperser which may be used to disrupt the oleaginous microorganism according to the exemplary embodiment of the present invention may include the oleaginous microorganism impinging plate 500 and the high-pressure supply part 400 which may inject gas into the acceleration nozzle part 300 at a high pressure.

That is, the exemplary embodiment of the present invention may be a method for producing bio-oil by allowing the cultivated oleaginous microorganism to impinge on the impinging plate 500 using the supersonic disperser under the presence of gas to disrupt the cultivated oleaginous microorganism.

Further, the supersonic disperser used in the disruption process according to the exemplary embodiment of the present invention includes the high-pressure supply part 400 which may inject gas into the acceleration nozzle at a high pressure.

The pressure of the high-pressure supply part 400 according to the exemplary embodiment of the present invention may be maintained so that the gas injected into the acceleration nozzle part 300 of the supersonic disperser is maintained at a high pressure enough to ultrasonically accelerate the oleaginous microorganism.

In more detail, the pressure in the high-pressure supply part 400 may be 1 to 2 MPa.

The oleaginous microorganism disruption process according to the exemplary embodiment of the present invention directly injects the oleaginous microorganism cultivated by the fermentor 100 into the acceleration nozzle part 300 by the culture medium transfer pump 200 without the separate drying process, thereby continuously producing the bio-oil from the oleaginous microorganism in an economical and simple process condition.

The gas used in the disruption process according to the exemplary embodiment of the present invention may be inert gas or active gas, and therefore any gas may be used as long as gas may achieve the object of the present invention. Preferably, air, nitrogen, carbon dioxide, helium, etc., may be used.

In the disruption process according to the exemplary embodiment of the present invention, the supply speed of gas injected into the acceleration nozzle part 300 of the supersonic disperser is enough to ultrasonically accelerate the oleaginous microorganism under the high pressure condition.

In more detail, the supply speed of gas injected into the acceleration nozzle part 300 of the supersonic disperser in the high-pressure supply part 400 according to the exemplary embodiment of the present invention may be 0.5 to 3 MPa, more preferably 1 to 2 MPa.

As the impinging plate 500 according to the exemplary embodiment of the present invention, a metal plate which has a large disruption effect of the oleaginous microorganism, no disruptions deposited thereon, and a smooth surface. Preferably, a surface of the metal plate is coated with diamond, thereby increasing strength against impingement and abrasion.

As described above, the disruption process according to the exemplary embodiment of the present invention ultrasonically accelerates the oleaginous microorganism using gas to induce the reduction in temperature due to the heat insulation expansion and allows the oleaginous microorganism to impinge on the impinging plate in the state in which a cell surface of the oleaginous microorganism is hard to generate an impulsive force and/or a shearing force, etc., thereby achieving a disruption rate higher than that of other disruption processes.

The oleaginous microorganism which goes through the disruption process according to the exemplary embodiment of the present invention may go through the extracting of the bio-oil. All the methods for extracting bio-oil which may achieve the object of the present invention may be used. Among those, a solvent extraction method using a solvent is preferable.

In the oleaginous microorganism disruption solution which goes through the disruption process according to the exemplary embodiment of the present invention, the disruption rate of the cell wall is very high and therefore an amount of bio-oil which may be extracted by the solvent extraction method may be more increased than the other existing disruption and extraction processes.

As the extraction solvent used in the extraction process according to the exemplary embodiment of the present invention, an organic solvent is preferable. Herein, a polar organic solvent and a non-polar organic solvent may be used without any limitation as long as the extraction solvent is a kind of organic solvent.

For example, the extraction solvent may be any one selected from a group consisting of hexane, methanol, ethanol, butanol, isopropanol, chloroform, acetone, and acetonitrile, and a mixture thereof.

In addition, the solvent extraction method may be performed by a soxhlet extraction device, an agitation extraction device, etc., but is not limited thereto. Therefore, any device which may achieve the object of the present invention may be used without limitation.

An extraction solution including the oleaginous microorganism which goes through the disruption process and the extraction process according to the exemplary embodiment of the present invention may be separated into an oil phase including the bio-oil and an aqueous phase including the cell disruptions and the bio-oil may be produced by recovering and purifying only the oil phase after the extraction process is completed.

The method for producing bio-oil according to the exemplary embodiment of the present invention may be the method for producing bio-oil which further includes separating the oil phase from the aqueous phase in the oleaginous microorganism extraction solution which goes through the disrupting and the extracting.

The extracted and separated material is the bio-oil prior to being purified and the final bio-oil product may be acquired by a series of bio-oil purifying processes.

That is, the present invention may be the method for producing bio-oil which further includes purifying the extracted and separated bio-oil.

The bio-oil produced from the oleaginous microorganism according to the exemplary embodiment of the present invention preferably includes a large amount of omega-3 unsaturated fatty acid, more preferably contains omega-6 unsaturated fatty acid in addition to the large content of omega-3 unsaturated fatty acid.

Therefore, the purifying of the bio-oil which goes through the extracting and the separating according to the exemplary embodiment of the present invention may include all the processes of producing the final bio-oil products containing a large amount of omega-3 unsaturated fatty acid and omega-6 unsaturated fatty acid.

As a non-restrictive example, the purifying of the bio-oil according to the exemplary embodiment of the present invention includes at least one selected from removing coagulated oil, bleaching using at least one of bleaching clay and active carbon, filtering, and deodorizing.

In more detail, in the purifying of the bio-oil according to the exemplary embodiment of the present invention, the removing of the coagulated oil removes the coagulated oil using silica gel, etc. For example, the coagulated oil may be removed by being left at a temperature condition of −5 to 0° C. for 5 to 20 hours.

Further, in the bleaching, the bio-oil which goes through the extracting and the separating may be purified using at least any one selected from bleaching clay, active carbon, kaolinite, zeolite, and bentonite.

In the bleaching, the used materials may serve as an adsorbent and may also serve to remove humidity, smell, and pollutants such as heavy metal.

The filtering may be performed using a filter having a pore size of 0.5 to 1 μm and the deodorizing may be performed by a pressure-reducing vapor deodorizing process but is not limited thereto.

The final bio-oil product produced by the purifying of the bio-oil according to the exemplary embodiment of the present invention may contain a large amount of omega-3 unsaturated fatty acid and omega-6 unsaturated fatty acid. Preferably, the omega-3 unsaturated fatty acid and the omega-6 unsaturated fatty acid may be equal to or more than 30 wt % in of a total content of bio-oil, more preferably, equal to or more than 40 wt %, and most preferably, equal to or more than 50 wt %.

The oleaginous microorganism cultivating process and the oleaginous microorganism disrupting process using a supersonic disperser according to the example of the present invention and the method for bio-oil using the same will be described below, but the following examples embodiment is only example of the technical spirit of the present invention and therefore it is apparent to those skilled in the art that the scope of the present invention is not limited to the following exemplary embodiments.

[Example 1] Cultivating of Oleaginous Microorganism

The oleaginous microorganism *thraustochytrium* sp. divided from American Type Culture Collection (ATCC) was cultivated by the batch manner under the condition of 100 rpm, 1 vvm, and pH 7 at 28° C. for 72 hours in a 3 L of culture medium (5 L jar fermentor) to which 60 g/L of glucose, 6 g/L of yeast extract, 25 g/L of bay salt are added.

[Example 2] Disrupting of Cultivated Oleaginous Microorganism

After the culture medium cultivated according to Example 1 was recovered, the recovered culture medium was injected into the acceleration nozzle part of the supersonic disperser at a speed of 100 ml/min by the culture medium transfer pump and the oleaginous microorganism cultivated by injecting the compressed air at a pressure of 1 MPa was ultrasonically accelerated. The oleaginous microorganism ultrasonically accelerated by the compressed air impinged on the impinging plate and the disrupted oleaginous microorganism was transferred to the extraction and separation part. The microscopic examination results of the disruption solution by the microscope were illustrated in [FIG. 3]. It was confirmed that the disruption solution is disrupted beyond about 95% in the case of using the supersonic disperser according to the present invention.

[Comparative Example 1] Disrupting of Oleaginous Microorganism Using Ultrahomogenizer After the culture medium cultivated according to Example 1 was recovered, 500 ml of recovered culture medium was injected into the ultrahomogenizer. Next, the oleaginous microorganism was disrupted by pressing the ultrahomogenizer at 30,000 to 35,000 psi. The disruptions were again injected into the ultrahomogenizer and again disrupted under the above condition, which was repeated three times. The disruptions recover part recovered the disruptions while cooling disruptions using the cooling water of 10° C. The microscopic examination results of the disruption solution by the microscope were illustrated in [FIG. 4]. It was confirmed that the disruption rate of the oleaginous microorganism is about 90% in the case of using the ultrahomogenizer.

[Comparative Example 2] Disrupting of Oleaginous Microorganism by Microwave

After the culture medium cultivated according to Example 1 was recovered, the recovered culture medium was taken as much as 500 ml, was put in 1000 L of glass container, and treated for 5 to 10 minutes by the microwave. After the disruption solution was cooled at room temperature, the microscopic examination results of the disruption solution by the microscope were illustrated in [FIG. 5]. It was confirmed that the disruption rate of the oleaginous microorganism is about 70% in the case of using the microwave.

[Comparative Example 3] Disrupting of Oleaginous Microorganism Using Ultrasonication After the culture medium cultivated according to Example 1 was recovered, the recovered culture medium was taken as much as 500 ml, was put in 1000 L of glass container, and treated for 30 minutes by 20 seconds at an interval of 10 seconds by ultrasonication of 35 to 40 kHz. To prevent the temperature of the culture medium from rising, the sample container was put in an ice container and then was subjected to the ultrasonic treatment. It was confirmed that as the microscopic examination results of the disruption solution by the microscope, the oleaginous microorganism was disrupted as much as about 70% as illustrated in [FIG. 6].

Comparing the disruption rates of the disruption solutions according to Example 2 and Comparative Examples 1 to 3 as shown in the following [Table 1], it could be confirmed that the efficiency of the disruption process using the supersonic disperser according to the exemplary embodiment of the present invention is high.

TABLE 1

| | Comparison of disruption rate of oleaginous microorganism depending on disruption methods | | | |
|---|---|---|---|---|
| | Disruption method | | | |
| | Supersonic disperser | Ultra-homogenizer | Microwave | Ultra-sonication |
| Disruption Rate (%) | 95 | 90 | 70 | 70 |

[Example 3] Extracting of Bio-Oil from Oleaginous Microorganism Disruption Solution 100 ml of oleaginous microorganism disruption solution acquired according to Example 2 and Comparative Examples 1, 2, and 3 was put in different containers and 10 ml of hexane which is the extraction solvent was put in different containers. Next, the mixture was agitated at a speed of 150 to 200 rpm for 30 minutes for extraction. After an agitation solution was centrifuged at 6000 rpm for minutes, the liquid phase was transferred to a fractional funnel, left for 30 to 60 minutes, and separated into the oil phase and the aqueous phase. When the liquid phase is not completely separated and emulsion of water and oil occurs, 4 to 5 ml of iso-propyl alcohol was injected, agitated, and stayed, and the water and the oil was easily separated. The oil phase was acquired, the hexane was evaporated in a drier of 60 to 80° C., and then only the bio-oil was acquired and quantified. The acquired amount of bio-oil is different depending on the oleaginous microorganism fungi disruption technology as shown in [Table 2]. As the fungi disruption was made well, the yield of the bio-oil was getting higher.

TABLE 2

Comparison of amount of bio-oil extracted from disruption solution of oleaginous microorganism depending on disruption methods

| | Disruption method | | | |
|---|---|---|---|---|
| | Supersonic disperser | Ultra-homogenization | Microwave | Ultra-sonication |
| Acquired oil amount (g) | 2.54(±0.08) | 2.41(±0.03) | 1.77(±0.26) | 1.72(±0.21) |

As described above, the oleaginous microorganism disruption process according to the exemplary embodiment of the present invention has the disruption rate higher than that of the processes of ultrahomogenization, microwave, ultrasonication, etc., thereby acquiring the bio-oil at the higher yield.

The invention claimed is:

1. A method for producing bio-oil without a separate dewatering process, comprising: cultivating oleaginous microorganism; ultrasonically accelerating the cultivated oleaginous microorganism using gas supplied at a pressure high enough to disrupt the oleaginous microorganism by impinging on an impinging plate; and extracting the bio-oil from the disrupted oleaginous microorganism wherein the high pressure ranges from 0.5 to 3 MPa.

2. The method of claim 1, wherein in the cultivating, the oleaginous microorganism is cultivated in batch, fed-batch, or continuous fermentor.

3. The method of claim 1, wherein in the ultrasonically accelerating of the oleaginous microorganism to disrupt the oleaginous microorganism, the oleaginous microorganism is disrupted by impinging on an impinging plate having a smooth surface using a supersonic disperser.

4. The method of claim 3, wherein the supersonic disperser includes a high-pressure supply part supplying the gas into an acceleration nozzle.

5. The method of claim 4, wherein the gas is any one selected from air, nitrogen, carbon dioxide, and helium.

6. The method of claim 3, wherein the extracting step comprises a solvent extraction method.

7. The method of claim 6, further comprising: after the extracting step, separating the bio-oil from an aqueous phase.

8. The method of claim 7, further comprising: purifying the extracted and separated bio-oil.

9. The method of claim 8, wherein the purifying includes at least one selected from removing coagulated sebum, bleaching using at least one of bleaching clay and active carbon, filtering, and deodorizing.

10. The method of claim 7, wherein the bio-oil includes omega-3 unsaturated fatty acid.

11. The method of claim 10, wherein the omega-3 unsaturated fatty acid is equal to or more than 30 wt % of a total content of the bio-oil.

12. The method of claim 1, wherein the bio-oil includes omega-3 unsaturated fatty acid.

13. The method of claim 12, wherein the omega-3 unsaturated fatty acid is equal to or more than 30 wt % of a total content of the bio-oil.

\* \* \* \* \*